United States Patent [19]

Hjortsberg et al.

[11] Patent Number: 5,736,028
[45] Date of Patent: Apr. 7, 1998

[54] SENSOR AND METHOD FOR DETECTING OXIDES OF NITROGEN

[75] Inventors: Ove Hjortsberg, Göteborg; Staffan Lundgren, Hindås; Ulf Arlig, Billdal, all of Sweden

[73] Assignee: AB Volvo, Sweden

[21] Appl. No.: 640,839

[22] PCT Filed: Nov. 8, 1994

[86] PCT No.: PCT/SE94/01050
§ 371 Date: Jul. 24, 1996
§ 102(e) Date: Jul. 24, 1996

[87] PCT Pub. No.: WO95/13533
PCT Pub. Date: May 18, 1995

[30] Foreign Application Priority Data

Nov. 8, 1993 [SE] Sweden ................................. 9303664

[51] Int. Cl.$^6$ ................................................ G01N 27/407
[52] U.S. Cl. ............................ 205/781; 204/424; 204/425; 204/426; 204/428; 205/783.5; 205/784.5
[58] Field of Search ....................... 204/421–429; 205/781, 783.5, 784, 784.5, 785; 422/98

[56] References Cited

U.S. PATENT DOCUMENTS 4,863,584  9/1989  Kojima et al. .
4,913,792  4/1990  Nagata et al. .................. 204/426
4,927,517  5/1990  Mizutani et al. .
5,034,112  7/1991  Murase et al. .
5,217,588  6/1993  Wang et al. ................... 205/781
5,397,442  3/1995  Wachsman .................... 205/781
5,409,591  4/1995  Baker et al. ................... 205/781
5,417,100  5/1995  Miller et al. ................... 204/424

OTHER PUBLICATIONS

Orbit Search Service, File WPAT, Accession No. 93-031766/04, Mitsubishi Motor Corp., JP04359144-A, 91.12.11 (9304) 4p, abstract.

Primary Examiner—T. Tung
Attorney, Agent, or Firm—Lerner, David, Littenberg, Krumholz & Mentlik

[57] ABSTRACT

The present invention relates to a sensor for detection of oxides of nitrogen forming part of a gas, including a substrate consisting of a solid electrolyte on which a conductive pattern is arranged which includes at least two parts forming an anode and a cathode, a current being produced in the sensor in the presence of oxides of nitrogen and the anode and the cathode being connected to an external voltage source which is adapted to drive the current and to means for measuring the current, which constitutes a measure of the concentration of oxides of nitrogen in the gas. The sensor is adapted to generate the current by means of a transport of oxygen ions in the sensor which essentially originates from oxides of nitrogen being part of the gas, independently from the content of oxygen in the gas.

12 Claims, 4 Drawing Sheets

SENSOR AND METHOD FOR DETECTING OXIDES OF NITROGEN

The present invention relates to a sensor for detection of oxides of nitrogen in accordance with the preamble of appended claim 1. The invention also relates to a use of a sensor in accordance with claim 9 and a method for detection of oxides of nitrogen in accordance with appended claim 10.

In connection with combustion processes, particularly in environments having high concentrations of oxygen, it would be advantageous to use a sensor for detection of oxides of nitrogen ("$NO_x$ compounds") in the combustion exhaust gases.

In particular, such a sensor ("$NO_x$ sensor") may be utilized in motor vehicles and may preferably be arranged in connection with a catalytic converter in the motor vehicle. Such a $NO_x$ sensor could be adapted to emit an output signal which indicates the concentration of $NO_x$ compounds in the exhaust gases. If the $NO_x$ sensor is arranged upstream of the catalytic converter, this output signal can be used to minimize the emission of $NO_x$ compounds by controlling the operation of the engine.

A device for detection of $NO_x$ compounds is previously known from U.S. Pat. No. 4,816,749, which device comprises a substrate 1 which may be a ceramic material. The device also comprises a cathode 2 which may have a section 7 consisting of porous gold serving as a "diffusion barrier", and an anode 3. Furthermore, the device comprises a solid electrolyte 4. The $NO_x$ compounds contained in the surrounding gases may diffuse through the cathode 2 and be transported through the electrolyte 4 towards the anode 3. The electric current thus produced may be recorded by means of a measuring instrument 6.

A disadvantage with the device according to U.S. Pat. No. 4,816,749 is that it cannot produce a precise measurement of the concentration of $NO_x$ compounds in the surrounding gases, but only an indication, e.g. an alarm signal, when a certain concentration (corresponding to a certain predetermined limit level) of $NO_x$ compounds is present.

The object of the invention is to provide an improved sensor for detection of oxides of nitrogen, in particular in connection with exhaust gas systems in vehicles. This is accomplished by means of a device of the above-mentioned kind, the features of which will be apparent from claim 1.

The device in accordance with the invention allows an accurate measurement of the concentration of $NO_x$ compounds. This is carried out with a short response time and a high selectivity for $NO_x$ compounds when measuring in gases with high levels of oxygen. The device allows a continuous measurement of the $NO_x$ concentration, in contrast to the device according to the above-mentioned US document which may only give an indication when a certain level has been reached.

By means of its construction, the device according to the invention is thermally and mechanically stable and thereby suitable for use in both mobile and fixed combustion apparatus. Furthermore, it is cheap and allows simple mass production, which makes it possible to mount it on mass produced motor vehicles and to arrange it for emitting a signal containing a measure of the concentration of $NO_x$ compounds in the exhaust gases, to a control unit arranged in the vehicle.

In accordance with a preferred embodiment, the invention comprises means for heating thereof to a suitable working temperature. This provides a stable and uniform operation in connection with detection of $NO_x$ compounds.

In accordance with a further embodiment, the device may be provided with a heat stabilizing protective cover, which to a high degree renders the signal from the sensor independent of fluctuations in the temperature of the surrounding gas.

BRIEF DESCRIPTION OF THE DRAWINGS

The invention will be described in the following with reference to a preferred embodiment and the annexed drawings, in which

FIG. 1 shows a view of one of the faces of a sensor 1 for detection of oxides of nitrogen in accordance with the present invention. In particular, the invention is primarily intended for use in detection of nitrogen oxide (NO) and nitrogen dioxide ($NO_2$). The sensor 1 comprises a substrate in the form of a plate 2 manufactured from a solid electrolyte, preferably zirconium dioxide, which has the property of being a good conductor of oxygen ions at the temperatures (approximately 600°–700°) at which the invention normally has its use. Bismuth dioxide may also be used as a material for the plate 2.

Figure 1:
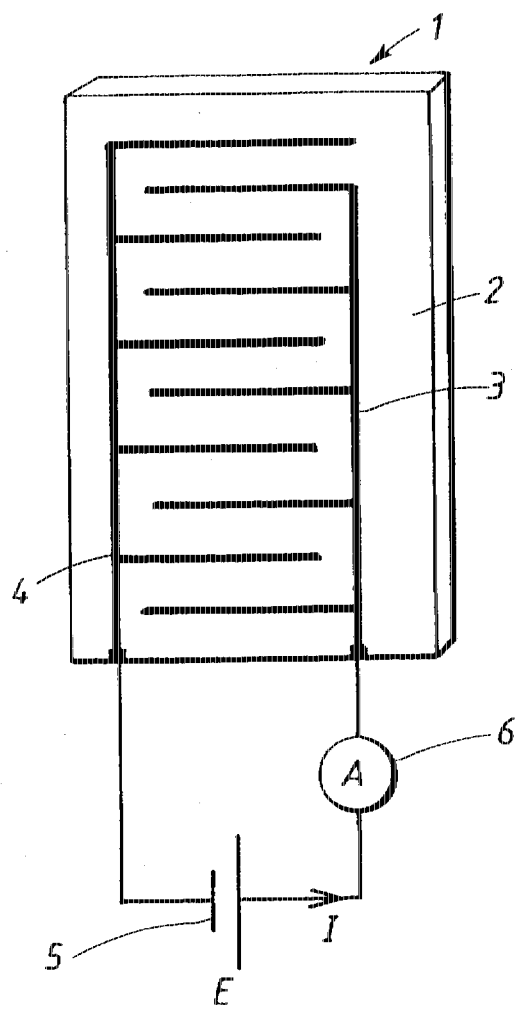
FIGS. 1 and 2 show the front and the rear faces, respectively, of a device in accordance with the present invention.

The zirconium dioxide is preferably stabilized, i.e. it is "fixed" in a certain crystal structure which is suitable with regard to its ability to conduct oxygen ions. Yttrium oxide or calcium oxide may be used as a stabilizer.

The plate 2 is coated with a conductive pattern 3, 4 consisting of a layer of metal, preferably gold. The gold is preferably porous, i.e. it has a slightly "non-homogenous" and "sponge-like" structure.

The conductive pattern 3, 4 is formed with a first conductive path 3 which functions as an anode, and a second conductive path 4 which functions as a cathode. The anode 3 can be made from some other material than gold, for example platinum, rhodium, palladium or iridium.

When the sensor is surrounded by a gas which contains $NO_x$ compounds, these compounds will be absorbed on the surface of the sensor 1, i.e. on the plate 2 and on the anode 3 and the cathode 4. Thereafter, a selective dissociation, i.e. a decomposition, takes place so that negative oxygen ions, $O^-$, are produced at the cathode 4.

A first-voltage source 5 is connected to the anode 3 and the cathode 4. By means of the voltage E supplied from the voltage source 5, the oxygen ions are transported through the oxygen ion-conducting plate 2 from the cathode 4 to the anode 3.

Molecular oxygen, $O_2$, is produced at the anode 3, which desorbs from the surface of the sensor 1 and back into the gas phase. At the same time as the oxygen atoms are ionized at the cathode 3 the nitrogen atoms recombine into molecular nitrogen, $N_2$, and return from the surface of the sensor 1 into the gas phase.

In the electric circuit consisting of the plate 2, the anode 3 and the cathode 4 as well as the first voltage source 5, an ammeter 6 is arranged for measuring the oxygen ion current I produced in the circuit. The measured current I constitutes a measure of the concentration of $NO_x$ compounds in the sensor's 1 environment.

The voltage E is preferably chosen so high that all the negative ions which are produced at the cathode 4 can be transported to the anode 3, thereby contributing to the current I. In this manner, a high measuring signal to the ammeter 6 is obtained.

During the tranport from the cathode 4 to the anode 3, the oxygen ions will essentially be transported along the surface layer of the plate 2. This gives a good time response during measurements with the sensor 1.

In order to accomplish an optimized transport of oxygen ions the anode 3 and the cathode 4 are each designed in the form of a straight line with a plurality of transverse line which are arranged so that they project essentially perpendicularly to the straight line. The two conductive patterns 3, 4 are arranged so that they "protrude into each other". By means of this arrangement, the boundary surface between the electrodes 3, 4, respectively, and the plate 2 where transport of negative oxygen ions occurs is as large as possible. This contributes to a high current I.

It is of utmost importance that the conductive paths 3, 4 are made as long as possible. This provides optimally large boundary layers between the conductive paths 3, 4, the plate 2 and the gas in which the sensor 1 is arranged. It is also of importance that the distance between the two conductive paths 3, 4 be as little as possible, which gives a short response time during measurements with the sensor 1.

Figure 2:
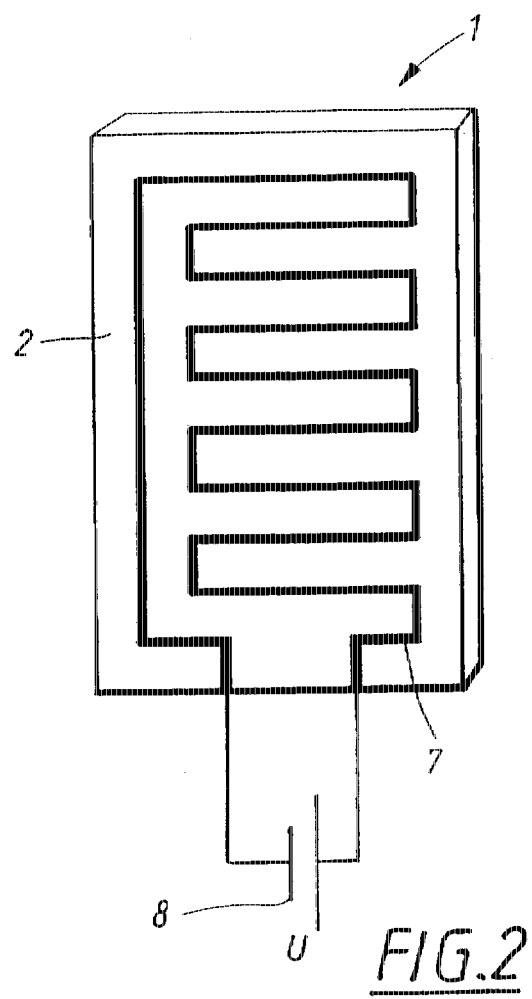

In FIG. 2, a flat view of the other side of a sensor according to the invention is shown. This side is provided with a heating wire 7 which consists of a suitable alloy and which is connected to a second voltage source 8. The voltage U of the second voltage source 8 is chosen so that the heating wire 7 can heat the plate 2 to the proper working temperature, at which the plate 2 is a conductor of oxygen ions. This makes it possible that the above-mentioned current I of oxygen ions may flow between the cathode 4 and the anode 3. In normal cases, the working temperature of the sensor 1 is approximately 600°–700° C.

Alternatively, it is possible to arrange a heating element or the like in connection with the sensor 1, for the heating thereof.

During use of the invention in combustion processes where the exhaust gases have a very high temperature, it is possible that the exhaust gases may heat the plate 2 to the temperature where there is a high conductivity of oxygen ions. Consequently, in this case there is no need for a heating wire 7 or a voltage source 8.

It should be noted that the heating wire 7 may be arranged on the same side of the plate i as the anode 3 and the cathode 4.

Figure 3:
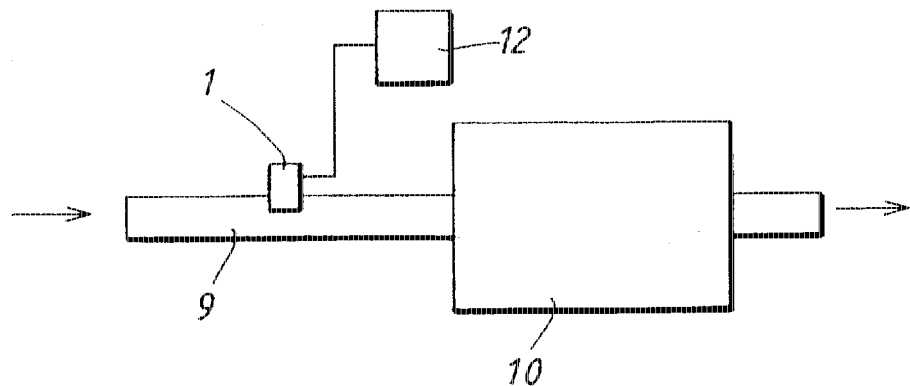
FIGS. 3, 4, 5 and 6 show how the device can be arranged in a vehicle.

In FIG. 3 there is shown how a sensor 1 according to the invention can be arranged in a motor vehicle. The exhaust gases from the vehicle's engine (not shown) are guided through an exhaust system 9, past the sensor 1 and to a catalytic converter 10 of conventional type. The sensor 1, which is connected to the voltage sources 5, 8 and the ammeter 6 (not shown in FIG. 3), emits a signal which is delivered to a control or measuring unit 12. This signal may thereafter be used for control of the operation of the engine for the purpose of minimizing the discharged $NO_x$ compounds.

Figure 4:
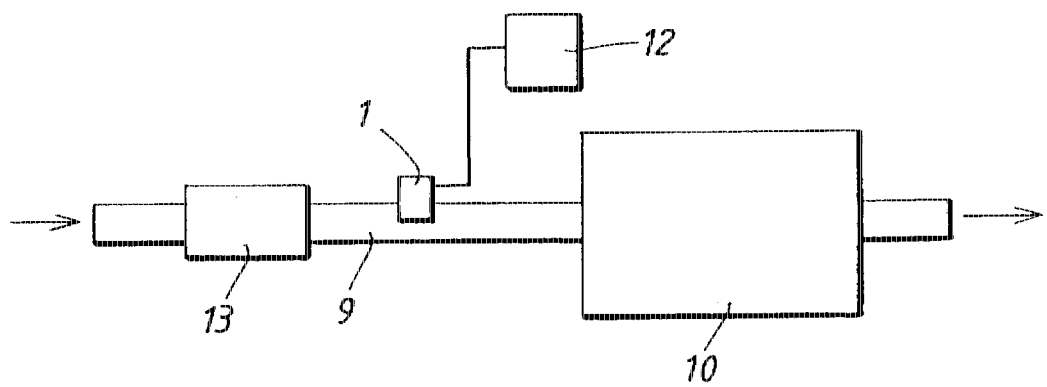

In FIG. 4 a further embodiment is illustrated, showing how a sensor 1 according to the invention may be placed in a motor vehicle. The sensor 1 is arranged downstream of an oxidation catalyst 13 for reducing the discharged HC and CO compounds, and which is particularly used in connection with petrol or diesel driven vehicles. In the oxidation catalyst 13, a combustion of HC and CO compounds (to $CO_2$ and $H_2O$) takes place so that these gases do not influence the accuracy of the measuring signal emitted by the sensor 1 in connection with the detection of $NO_x$ compounds. In this manner, a high selectivity for $NO_x$ compounds is accomplished during measurements with the sensor 1. A catalytic converter 12 is arranged downstream of the sensor 1.

Figure 5:
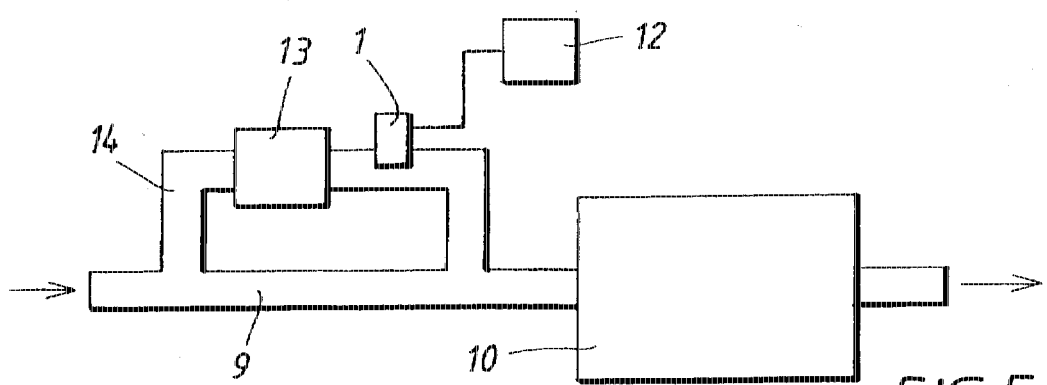

FIG. 5 shows how the sensor 1 may be arranged in a branch conduit 14 of an exhaust system 9. Upstream of the sensor 1 an oxidation catalyst 13 of the above-mentioned type is preferably arranged. The exhaust gases in the branch conduit 14 downstream of the oxidation catalyst 13 contain $N_2$, $O_2$, NO, $CO_2$ and $H_2O$, which is a gas composition in which the sensor 1 may operate satisfactorily.

The sensor 1 is highly selective for $NO_x$ compounds as opposed to oxygen (i.e. the oxygen ions causing the current I originate mainly from $NO_x$ compounds and not from molecular oxygen in the exhaust gases) which means that low concentrations of nitrogen oxide, in the region of a few hundred ppm, may be detected in oxygen-rich gases. Any oxygen in the exhaust gases (it should for example be noted that diesel exhaust gases contain 5–20% oxygen) can adsorb, dissociate and be ionized on the surface and may contribute to the ion current I being measured by the ammeter, but due to the high selectivity for nitrogen oxide this contribution is however of insignificant magnitude.

Figure 6:
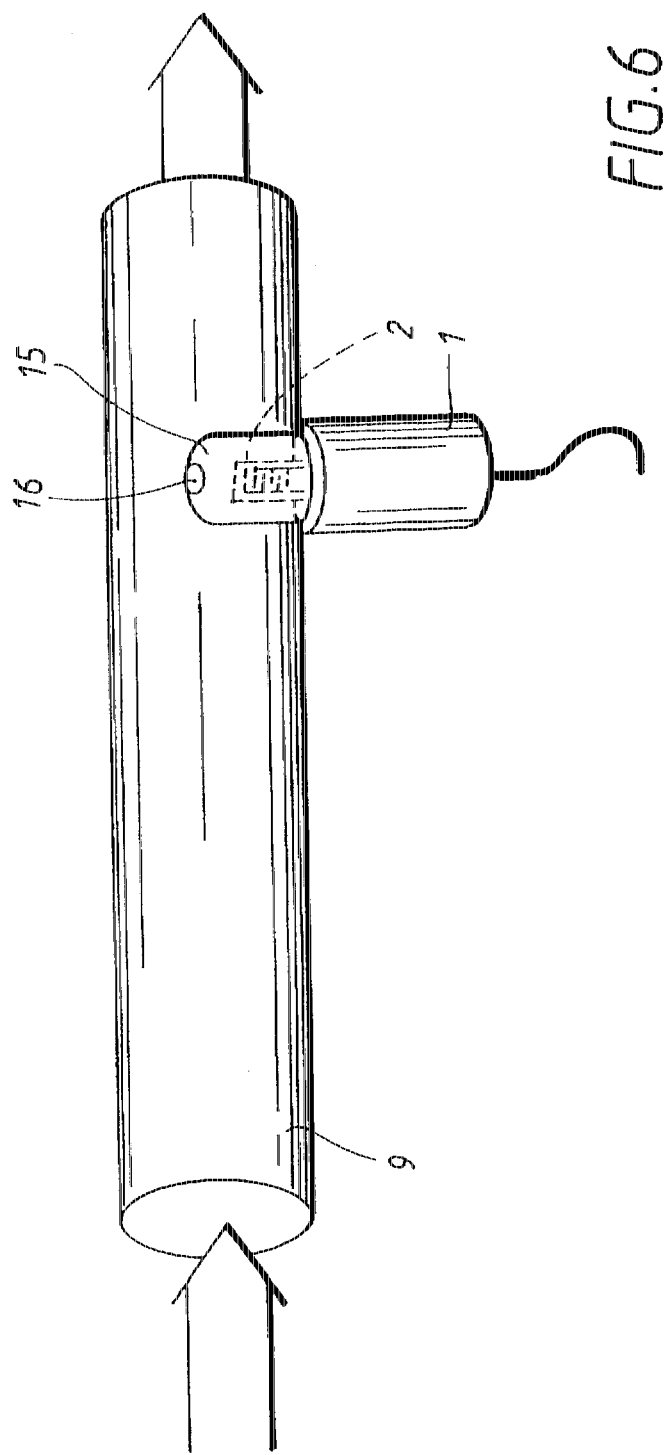

FIG. 6 shows a part of an exhaust gas system 9 of a motor vehicle. A sensor 1 is arranged in the exhaust gas system 9, and a protective cover 15 is provided over the plate 2 of the sensor 1. This protective cover 15 reduces the cooling effect which may be caused by the flowing exhaust gases, thereby allowing a high and uniform temperature inside the protective cover 15. The protective cover 15 is provided with at least one hole 16, alternatively at least one slit or the like, in order to expose the plate 2 to the exhaust gases. These holes 16 or slits may be arranged in a number of ways, for example at the top of the protective cover 15.

An arrangement with a sensor 1 in combination with a protective cover 15 implies that the operation of the sensor 1 is highly independent of the temperature of the surrounding gas.

Figure 7:
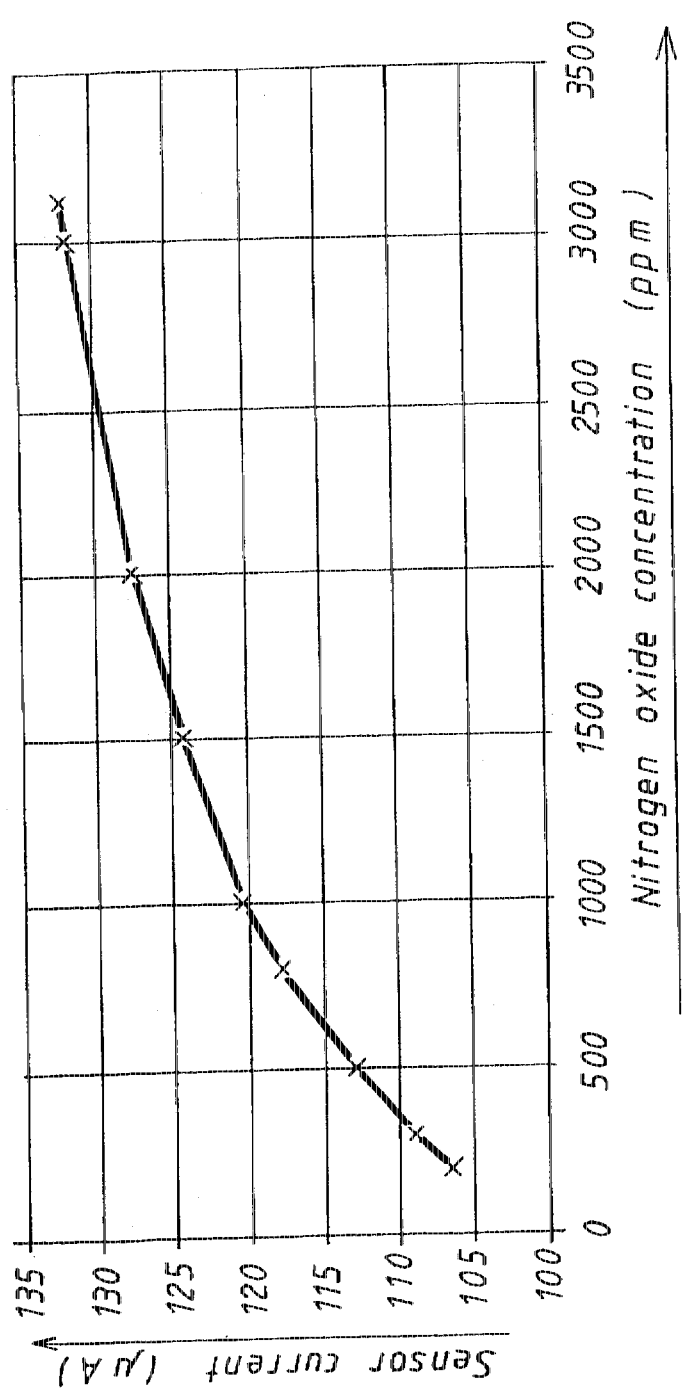
FIG. 7 is a diagram showing the relation between a measured current I and the concentration of oxides of nitrogen.

FIG. 7 is a diagram which shows the relationship between the concentration of $NO_x$ compounds (measured in ppm) and the measured current I. The diagram shows a measurement which has been carried out in a gas containing 20% oxygen.

During experiments it has become apparent that during the stationary measurements, i.e. when the sensor is exposed to a constant gas composition for a considerable time, the sensor has sufficient time to set itself to a stationary level at which the measured current I from the sensor is constant. If the concentration of nitrogen oxide in the gas changes, the current I also changes. The response time for the sensor, i.e. the time which is required for the current I to reach the correct value when the gas changes from one composition to another one, is less than one second. The resolution of the sensor, i.e. the smallest deviation in nitrogen oxide concentration which can be measured by the sensor, is less than 100 ppm.

The output signal is thus a function of the $NO_x$ concentration in the exhaust gases. The sensor 1 according to the invention can measure $NO_x$ concentrations in the range of ppm at an oxygen content in the exhaust gases from 0 to 20%.

The sensor according to the invention is primarily intended for detection of nitrogen oxide (NO) and nitrogen dioxide ($NO_2$), which are present in various combustion processes. Such processes can for example be in connection with diesel vehicles and stationary combustion processes, e.g. oil-fired heating plants.

The invention is not limited to that discussed above. Instead different embodiments are possible within the scope of the appended claims. For example, it should be noted that the sensor 1 does not have to be manufactured in the form of a plate, but other geometrical shapes are also possible, e.g. cylindrical shapes. Furthermore, the conductive pattern which constitutes the anode 3 and the cathode 4 may be designed in different ways, for example as two helically shaped parts.

The two conductive paths 3, 4 are preferably arranged on the same side of the plate 2, but a placing thereof on opposite sides of the plate 2 is also possible.

Even if the sensor 1 according to the invention provides measurement with a high selectivity for $NO_x$ compounds above oxygen, in certain applications there may be higher demands on the accuracy of the measurements. In these cases, a separate oxygen sensor may be arranged in connection with the sensor 1, which oxygen sensor may be utilized for measuring the oxygen concentration of the present gas. The signal from the oxygen sensor may then by used in order to correct the value of the $NO_x$ concentration which was supplied from the sensor 1. The correction may for example be carried out by allowing the measurement value from the oxygen sensor to constitute a basis for a certain correction factor which depends on the oxygen concentration. By means of a computer-based evaluation unit, the measurement value relating to the $NO_x$ concentration may thereafter be corrected depending on the current oxygen concentration. In this manner, an improved measuring accuracy is obtained.

Finally, it should be noted that besides from the fact that a sensor may be arranged upstream of a catalytic converter 10, in accordance to what is shown in FIGS. 3–5, such a sensor 1 may also be arranged downstream of the catalyst 10. The output signal from such a sensor 1 which is arranged downstream may be utilized for control of the operation of the catalytic converter 10. Furthermore, an arrangement with two sensors according to the invention may be used, which sensors may be arranged upstream and downstream, respectively, of a catalytic converter 10 so that the combination of the measurement signals of these sensors may be utilized.

What is claimed is:

1. A sensor for detecting nitrogen oxides forming part of a gas comprising:
   a. a substrate, comprising a solid electrolyte;
   b. a conductive pattern arranged on said substrate comprising an anode and a cathode, said cathode comprising a metal which is highly selective for the dissociation of nitrogen oxides as compared to oxygen, whereby a current is generated by the transport of oxygen ions dissociated from said nitrogen oxides;
   c. an external voltage source connected to said anode and said cathode, said external voltage source being adapted to drive the current between said anode and said cathode; and
   d. measuring means for measuring said current connected to said anode and said cathode, whereby the measurement of said current corresponds to a measurement of the concentration of the nitrogen oxides in the gas.

2. The sensor of claim 1 wherein said cathode comprises gold.

3. The sensor of claim 1, further comprising heating means for heating said substrate.

4. The sensor of claim 1, wherein said substrate comprises stabilized zirconium dioxide.

5. The sensor of claim 4, further comprising heating means for heating said substrate.

6. The sensor of claims 3 or 5, wherein said heating means comprises a heating wire arranged on said substrate, and including a second voltage source connected to said heating wire.

7. The sensor of claim 1, further including a protective cover arranged in connection with said substrate, said protective cover including an opening.

8. The sensor of claim 1, wherein said anode and said cathode each comprise at least one straight line and a plurality of transverse lines protruding substantially perpendicularly from said straight lines.

9. The sensor of any of claim 1, wherein said anode and said cathode are arranged on the same side of said substrate.

10. A method of using a sensor comprising a substrate which comprises a solid electrolyte, said electrolyte including a conductive pattern arranged thereon, said conductive pattern including at least two portions comprising an anode and a cathode comprising a metal which is highly selective for the dissociation of nitrogen oxides as compared to oxygen, whereby a current is generated by the transport of oxygen ions dissociated from said nitrogen oxides, said method comprising measuring the concentration of said nitrogen oxides in a gas independently from the oxygen content in said gas.

11. The method of claim 10, wherein said measuring of said concentration of said nitrogen oxides comprises arranging said sensor in said gas, connecting a voltage source to said anode and said cathode, detecting the current flowing from said cathode to said anode, and deriving the concentration of said nitrogen oxides in said gas.

12. The method of claim 11, further comprising the steps of measuring the oxygen concentration in the gas, and correcting said measuring of the current by the amount of concentration of oxygen to more accurately derive the concentration of nitrogen oxides in the gas.

* * * * *

UNITED STATES PATENT AND TRADEMARK OFFICE
CERTIFICATE OF CORRECTION

PATENT NO. : 5,736,028
DATED : April 7, 1998
INVENTOR(S) : Hjortsberg, et. al.

It is certified that error appears in the above-indentified patent and that said Letters Patent is hereby corrected as shown below:

Column 2, line 2, "he" should read --be--.

Column 2, line 47, "first-voltage" should read --first voltage--.

Column 3, line 9, "line" should read --lines--.

Column 3, line 46, "i" should read --1--.

Column 4, line 4, "12" should read --10--.

Column 6, line 27, delete "any of".

Signed and Sealed this

Twenty-fifth Day of August, 1998

Attest:

BRUCE LEHMAN

*Attesting Officer*     *Commissioner of Patents and Trademarks*